United States Patent [19]

Hounsfield

[11] 4,126,787
[45] Nov. 21, 1978

[54] RADIOGRAPHY

[75] Inventor: Godfrey N. Hounsfield, Newark, England

[73] Assignee: EMI Limited, Hayes, England

[21] Appl. No.: 860,722

[22] Filed: Dec. 15, 1977

Related U.S. Application Data

[60] Continuation of Ser. No. 751,799, Dec. 17, 1976, abandoned, which is a division of Ser. No. 544,799, Jan. 28, 1975.

[51] Int. Cl.² ..................... A61B 6/02; G01N 23/04
[52] U.S. Cl. ............................. 250/445 T; 250/360
[58] Field of Search ........................ 250/360, 445 T

[56] References Cited

U.S. PATENT DOCUMENTS 4,035,651  7/1977  LeMay .................... 250/445 T

*Primary Examiner*—Alfred E. Smith
*Assistant Examiner*—T. N. Grigsby
*Attorney, Agent, or Firm*—Cooper, Dunham, Clark, Griffin & Moran

[57] ABSTRACT

In a method of examining a body by means of penetrating radiation a source is arranged to provide a fan shaped spread of the radiation and a detector examines the intensity of a plurality of individual beams of radiation defined from the fan. The source and detector are orbited about the body so that the beams are provided at a plurality of angles relative to the body. In the associated processing, the data signals from the detectors are combined so that each combined signal relates to two beams 180° to each other in the orbital movement. A further selection is also made of the data signals so that they are provided to a further processing stage in sets for which each set is of data signals relating to beams which are substantially parallel to each other.

7 Claims, 7 Drawing Figures

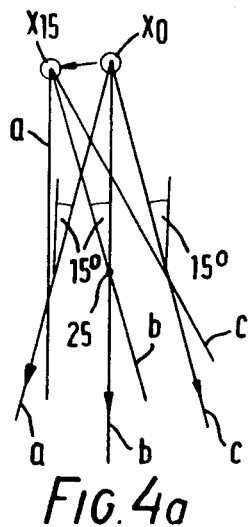
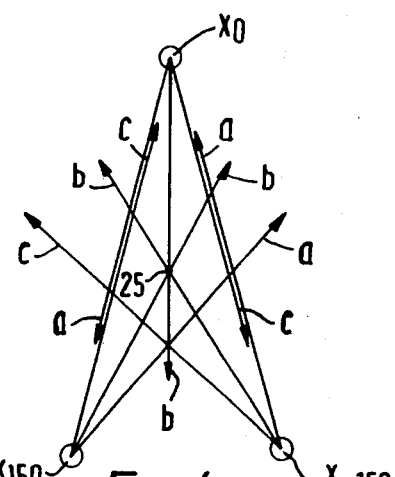
FIG.4a   FIG.4b
| | | |
|---|---|---|
| 15° | 0° | -15° |
| 30° | 15° | 0° |
| 45 | 30° | 15° |
| 60° | 45° | 30° |
| ⋮ | ⋮ | ⋮ |
| 165 | 150° | 135° |
| ±180° | 165° | 150° |
| -165° | ±180° | 165° |
| -150° | -165° | ±180° |
| -135° | -150° | -165° |
| ⋮ | ⋮ | ⋮ |
| -30° | -45° | -60° |
| -15° | -30° | -15° |
| 0° | -15° | -30° |
FIG.5

RADIOGRAPHY

This is a continuation of application Ser. No. 751,799 filed on Dec. 17, 1976 and now abandoned which in turn is a Divisional of Ser. No. 544,799 filed Jan. 28, 1975.

This invention relates to a method of and apparatus for examining a body by means of radiation such as X or Y radiation.

The method and apparatus according to the invention can be used to assist in the production of radiographs in any convenient form, such as a picture on a cathode ray tube or other image forming device, a photograph of such a picture, or a map of absorption coefficients such as may be produced by a digital computer and on which contours may subsequently be drawn.

In the method of, and apparatus, for examining a body described in U.S. Pat. No. 3,778,614 radiation is directed through part of the body, from an external source, in the form of a pencil beam. A scanning movement is imposed on the beam so that it takes up in turn a large number of differing dispositions, and a detector is used to provide a measure of the absorption of the beam in each such disposition after the beam has passed through the body. So that the beam takes up these various dispositions the source and the detector are reciprocated in a plane and are orbited about on axis normal to the plane. The various impositions thus lie in a plane through the body over which the distribution of absorption coefficient for the radiation used is derived by processing the beam absorption data provided by the detector. The processing is such that the finally displayed distribution of absorption is the result of successive approximations.

The method and apparatus in the aforesaid U.S. Pat. has proved to be successful for producing cross-sectional representation of parts of the living body, such as the head.

The arrangement described in the aforesaid specification for carrying out the scanning operation is however relatively slow and for scanning some parts of the body a much faster scanning rate is desirable. Apparatus capable of achieving a faster scanning rate is described in U.S. Pat. No. 3,999,073 filed Dec. 12, 1974 (Hounsfield et al) and according to this application the derivation of the absorption data signals is achieved by directing a fan-shaped spread of X-rays through the body and providing a bank of detectors at the other side of the body to measure the radiation transmitted along a set of beam paths within the fan. The fan shaped spread subtends an angle sufficient to include the whole region of interest in the plane of the body, so that a complete scan can be effected merely by orbiting the source and the detectors about the body.

In U.S. Pat. No. 3,924,129 there is described an apparatus for processing the absorption data by a convolution method. This latter method allows relatively faster processing than the iterative method of the said U.S. Pat. No 3,773,614.

According to one aspect of the invention there is provided an apparatus for examining a body by means of penetrating radiation such as X- cr γ- radiation, including source means for irradiating the body with a fan shaped spread of radiation, detector means comprising a plurality of detectors for detecting the radiation after passage through the body, each respective detector receiving radiation along a narrow but divergent beam path, means for scanning the source and detector means around the body so as to irradiate a planar section of the body along beams of said radiation at a plurality of angular positions in the plane of said section, so that a reconstruction of the distribution of absorption of the radiation in said section can be produced in response to beam data signals derived from the detectors, wherein absorption data signals representing the absorption of radiation along paths of substantially uniform width are produced by combining output signals relating to beam paths at angular positions substantially 180° apart.

According to another aspect of the invention there is provided a method of examining a body including the steps of irradiating the body with a fan shaped spread of penetrating radiation, such as X- or γ - radiation, scanning the source of the radiation and a detector means comprising a plurality of detectors sensitive to the radiation, around the body so as to irradiate a planar section of the body along beams of radiation at a plurality of angular positions in the plane of the section, combining beam data signals provided by said detector means related to beams of radiation at angular positions 180° apart to derive further data signals related to radiation along beam paths of substantially uniform width so that said further data signals can be processed to derive a reconstruction of the distribution of absorption of the radiation in the said section.

According to a further aspect of the invention there is provided an apparatus for examining a body by means of penetrating radiation such as X- or γ- radiation including source means arranged to irradiate a planar section of the body by means of a fan shaped spread of radiation in the plane of said section, detector means comprising a plurality of detectors arranged to determine the absorption suffered by said radiation after passage through the body along a plurality of angularly distributed beam paths in said fan, means for scanning the source and detector means around the body so as to irradiate the said section from a plurality of directions so that from the absorption beam data signals provided by said detectors, a reconstruction of the distribution of absorption of the radiation in said slice can be produced, wherein means are provided for selecting signals from said detectors, related to corresponding positions of said detectors in the scanning motion, to produce sequences of signals relating simply to parallel sets of beams of radiation.

In order that the invention may be clearly understood and readily carried into effect, the same will now be described with reference to the accompanying drawings in which:

FIG. 4a and 4b are diagrams used for explaining the invention,

FIG. 5 illustrates the arrangement of the absorption data in a preprocessing store and FIG. 6 illustrates a special circuit for arranging the absorption data in a form suitable in particular to the convolution processing.

Figure 1:
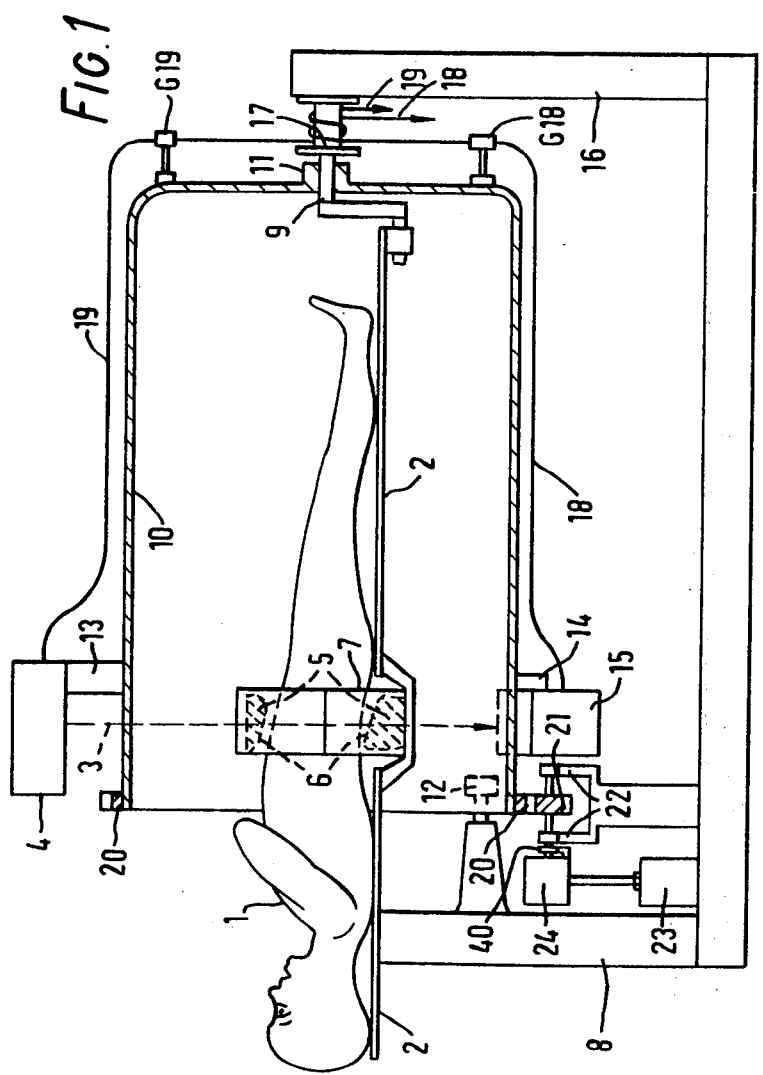
FIG. 1 shows the general layout in side elevation of an apparatus in accordance with the invention.

In FIG. 1 a patient 1 is shown lying on supporting means and his body is subjet to examination by X radiation indicated in broken line at 3. This radiation is generated by a source 4 and forms a fan shaped spread in a plane lying at right angles to the plane of the figure. It will be appreciated that the patient supporting means has to be sufficiently long to allow any desired section of the patients body to be located in the plane of the X-radiation.

In the region of the exploring radiation, the body of the patient is surrounded by a suitable medium which in this case is water, having an absorption coefficient for the radiation closely similar to that of body tissue. The water is shown in the figure at 5 and is contained within an envelope, or bag 6. The envelope 6 is positioned within a ring like structure 7 which may be of metal such as duralumin.

The ring member 7 is in two parts as described in U.S. Pat. No. 3,999,073 filed Dec. 12, 1974 (Hounsfield et al) and is in this example fixed to the supporting means 2. It should be noted that ring 7 may be mounted in movable relation to supporting means 2 if desired, to facilitate entry of the patient and further that supporting means 2 may be arranged to be movable in relation to other parts of the apparatus for the same purpose and for correct positioning in relation to the X-ray team.

Supporting means 2 is positioned at one end by a support 8 and at the other end by a fixing bracket 9. Bracket 9 is in the form of an axle member which has an axis about which the orbiting motion of the X-ray source 4 takes place, as will be made more clear.

Around the body of the patient when he is located in position in the apparatus there is disposed a surround or frame 10 which is cylindrical along its length having a longitudinal axis which is the axis of the bracket 9. At this end adjacent to this latter bracket it is closed and supported by a bearing 11 which, in turn, is supported by the axle of bracket 9. At its other end it is open to allow of positioning the patient within it, and at this end it is supported on rollers 12 which have suitable fixed bearings. These rollers are such that the surround member 10 is free to rotate on its axis, which as has been indicated is the axis about which the orbiting motion of the X-ray source 4 takes place. The source 4 is mounted on the surround member 10 by means of support 13. Directly opposite the source 4 there is mounted on the surround member 10, by means of a support 14, a detector means 15 so as to provide radiation absorption data from the body of the patient in the plane of the radiation from the source 4.

The axle of bracket 9 is carried by a support 16 and adjacent to that support and surrounding the axle is a bobbin 17. This last element is fixed to the support 16 and wound round it are cables 18 carrying absorption data from the detector means 15 to the processing unit and cables and connections 19 supplying power, control signals and cooling fluid to the X-ray source 4. With the orbiting motion of the source and detector means the cables wind on or off the bobbin 17 correspondingly. They are fed to the bobbin via guides G18 and G19 which are mounted on member 10. At the bobbin the cables and other connections are secured and thense pass to their respective connecting units, including the data processing unit mentioned, and a power supply unit.

For the purpose of achieving the orbiting motion the rim of surround member 10 at its open end is provided with gear teeth 20. Engaging with these teeth is a gear wheel 21, mounted on a shaft supported as shown by bearings 22. Gear wheel 21 is driven by a reversible motor 23 via a gearbox 24. It will be appreciated that gear teeth 20 may be provided at any desired position on member 10. A scanning timing signal unit 40 provides signals indicating the progress of the rotation of source 4. This may be a graticule on the shaft of gear 21 cooperating with a light source and photocell or alternatively a suitable cam arrangement.

Figure 2:
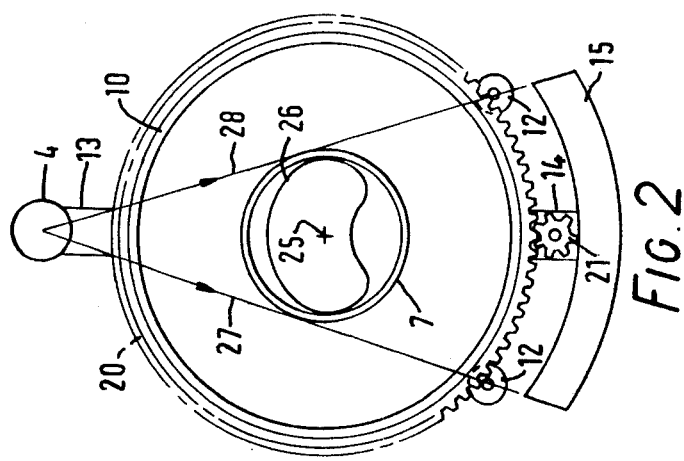
FIG. 2 illustrates the same apparatus in end elevation.

FIG. 2 as stated shows an end view of the apparatus illustrated in FIG. 1 and reference numerals have the same significance as in relation to FIG. 1. At 25 in FIG. 2 there is indicated the location of the orbital axis and 26 shows the outline of the cross-section of the patient's body in the plane of the exploring radiation.

FIG. 2 furthermore shows rays 27 and 28 indicating the extremes of the fan of radiation from source 4. It will be seen that the detector means 15 extends over the whole spread of the fan of radiation between rays 27 and 28. As explained in U.S. Pat. No. 3,973,128 (LeMay) means ray be provided to examine a desired region of the patients body in greater detail but no provision is made for that in the present example. In addition further details of the ring member 7 and associated retaining means are described in the said U.S. Pat. No.3,999,073 filed Dec. 12, 1974 (Hounsfield et al).

Figure 3:
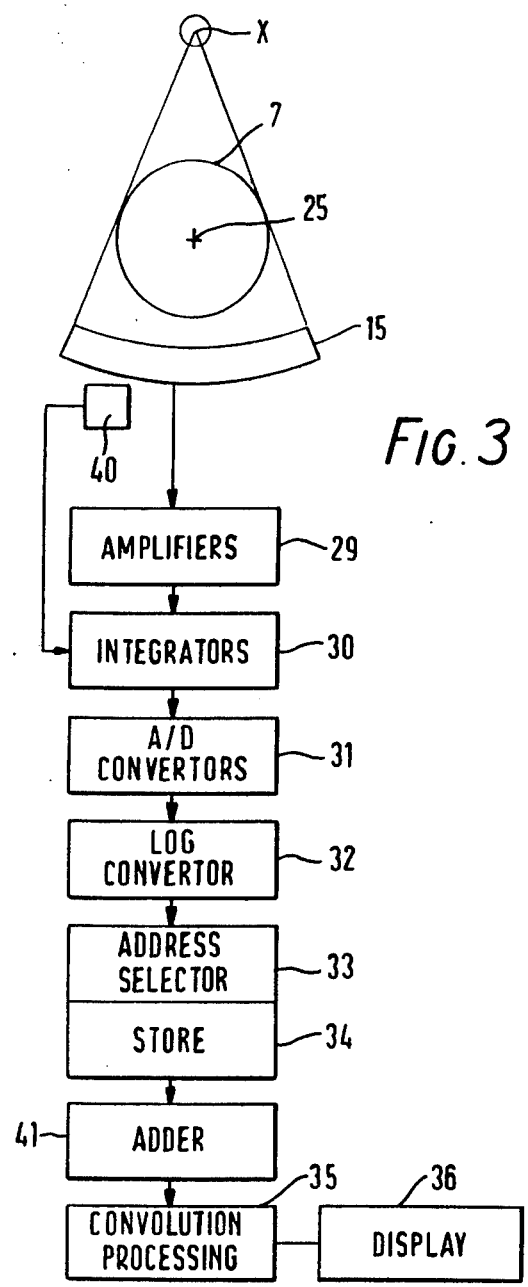
FIG. 3 shows in diagrammatic form the general layout of those parts of the apparatus concerned with processing of the absorption data.

FIG. 3 sets out diagrammatically the general arrangement of the processing for the apparatus shown in FIGS. 1 and 2.

In this figure the point X denotes the point of emission of X-radiation from the source 4, the point 25 the location of the orbital axis, 7 the location of the ring member and 15 the detector means providing absorption data for processing.

Detector means 15 includes a plurality of detectors and corresponding collimators defining individual beams of radiation as described in the aforesaid copending applications. In the course of the orbital movement of the apparatus the absorption data are obtained as output currents from the photomultipliers associated with the detectors. The data are amplified by respective amplifiers 29. The gains of the amplifiers are individually adjusted to compensate for the differing sensitivities of the various scintillation crystals of the detectors. If desired the gains of the amplifiers may be commonly controlled to compensate for any variations that may occur in the emission intensity of X-ray source 4. The currents as amplified are respectively integrated by Miller integrator circuits 30. The integrators are arranged, in response to timing signal unit 40 to operate for such a period that each individual beam corresponding to a detector extends over an angle of substantially 2/15°, in this example due to the orbital motions. Corresponding to this, the detectors are arranged at such a spacing that the centralines of those beams are at substantially 2/15° spacing, each being centred on point source X. The outputs of the integrators are converted from analogue to digital forms by converters 31.

It is desired that the final image reconstruction shall represent the distribution of the absorption coefficient over the area of the cross section under examination, the absorption coefficient being the absorption per unit length, in the immediate vicinity of a given joint, of an exploring beam passing the point. To achieve the desired result it is necessary that each output signal derived from the detector means 15 shall be converted to its logarithmic form. For this purpose log converter 32 operates on the digital data from A/D converters 31. Log converter 32 comprises logarithmic lock-up tables according to known usage. The data is written into a store 34 in response to an address selector 33, in a manner to be further described, and from there it is subject to convolution processing and interpolation in unit 35 before being displayed in a display and control unit 36. The operation and nature of processing unit 35 has been fully described in U.S. Pat. No. 3,924,129.

The technique described therein can be described as producing a corrected layergram and requires the data to be provided in sets each relating to a set of substantially parallel beams of radiation, the data of each set being proided term by term. Consequently address selector 33 and store 34, which can form part of a suitably programmed digital computer, are programmed to arrange the data into such "parallel" sets.

In the apparatus being described the integrators 30 operate for such a time that, considering the orbital motion during the integration period, the effective spread of the beam path is 2/15°, so that output signals are obtained after each 2/15° movement. Furthermore the spacing of beams in the fan is arranged so that the centrelines of adjacent beams are at substantially 2/15° spacing. Thus after each increment of rotation of this magnitude each beam will assume a position which is parallel to the position which one of its neighbours occupied prior to this increment of rotation. It is therefore possible by suitable selection of data from store 34 to produce signals corresponding to sets of parallel beams at 2/15° separation.

This is illustrated in FIG. 4 which shows a fan of three beams with centrelines at 15° spacing. The beams represent the centre and extreme beams of a 30° fan of beams but for the moment may be considered as if they are the only beams of a three beam fan. The three beams, designated $a$, $b$ and $c$ are illustrated in FIG. 4a, the corresponding detectors not being shown, for a position of the point source Xo for which centre beam $b$ makes an angle 0° with an arbitrary zero line vertical in the figure, and the other beam contrelines make the angles shown. It will be seen that when the source is orbited 15° to position $X_{15}$, corresponding to the beam centreline spacing, beam $a$ takes up a position parallel to the previous position of beam $b$ similarly $b$ becomes parallel to $c$. Beam $c$ takes up a new inclination. A further 15° movement will take beam $a$ parallel to the original position of beam $c$ etc. and thus sets of parallel beam positions are being built up.

Considering this it can be seen that if the data from converters 32 are directed into store 34 to locations labelled with an angular position for the corresponding beam, they can be extracted as sets of data for each such angle.

This is shown, for the illustrative set of three beams, in FIG. 5. The figure corresponds to a matrix of locations in store 34 with each such location being identified by the angle, relative to the arbitrary zero, of that beam for which the datum in the location was derived. Each detector provides data to elements of a column labelled $a$, $b$ or $c$ in correspondence with FIG. 4. As the centre beam ($b$) rotates through 360° all of the beams rotate through a series of angles including those shown. The 360° position, which is the same as 0°, is not shown. It will be understood also that $-180°$ is the same as $+180°$ and accordingly positive angles greater than 180° have been shown on the corresponding negative angles. The data are entered into the store in rows, each row corresponding to the mean angular position for one reading from each detector, as they are derived. For clarity not all rows have been shown. It can be seen that diagonal set of locations provide data for beams which are at the same angle and therefore parallel. It should be noted that although beams at the same angle are parallel they are not identical. The 0° set of beams, indicated by the solid diagonal line, forms a complete parallel set although the data must be obtained from the first rows and the last row. That set will, therefore, not be complete until all data has been derived. The data from the locations for such parallel sets are selected from store 34 and transferred serially to processor 35 for the convolution processing described in U.S. Pat. No. 3,924,129. The data may be transferred to processor 35 after all data has been derived and stored or, if desired, each "parallel" data set may be transferred as soon as it is completed. In the illustrative example of FIG. 5 the 15° set is the first to be completed.

In the present practical example of the apparatus illustrated in FIGS. 1 to 3 the store 34 has, of course, many more locations then that shown in FIG. 5. There are rows for each of the 2/15° orbital positions and a column for each of the detectors of detector means 15.

In regard to the arrangement of beams considered in U.S. Pat. Nos. 3,924,129 and 3,973,128 it is to be noted that the beams are in those cases implicity treated as though they are of uniform width. However, in the apparatus of FIG. 1 and 2, the beams defined by the detectors are not of this character, being narrower on the point X-ray source side of the explored field and wider on the detector side. The effect of this disparity is minimised in the apparatus described by not restricting the orbital motion to the 180° which would be in theory sufficient, but by continuing it for 360° so that for every beam disposition of the first 180° of scan there is a second which is identical except for the fact that the direction of passage of the radiation is reversed, and with it the sense of the disparity. The average of the two beam absorptions is then taken to produce data corresponding to a beam path of substantially uniform width considering the limited angular spread of each beam.

The use of two beams at 180° spacing to irradiate one beam path has the further advantage that the "skin dose" of radiation, resulting from the required total X-ray intensity for that path, is divided equally between surfaces at opposite ends of the path instead of being substantially concentrated at one end.

However it should be understood that data for each beam should be combined only with that for a beam at substantially 180° relation of scan. For a fan of beams, such as that of FIGS. 4 and 5, only data for the centre beam ($b$) can be combined with data for the same beam inverted so that data for the 180° set (broken diagonal line) is combined with that for the 0° set.

The position for the other beams of the set is shown in FIG. 4b. Three positions of the point source X are shown, identified by subscripts which represent the corresponding angular position of centre beam $b$. It will be seen that, for $X_{150}$, beam $c$ shares a beam path with beam $a$ of Xo and these may therefore be combined to give a uniform width beam. Similarly $c$ at Xo shares a path with $a$ at $X_{150}$. Considering this in relation to the storage location of FIG. 5 it can be seen that the 180° beam set data can be combined with the 0° data, provided the two sets are withdrawn from storage in inverse order. The combinations will thus be $(a_o + c_{180})$, $(b_o + b_{180})$ and $(c_o + a_{180})$.

For this purpose the digital computer forming address selector 33 and store 34 in FIG. 3 is arranged to derive the data from the locations in the manner described, combine them and transfer them to processor 35. For the purpose of this combination an adder 41 is provided between store 34 and processing unit 35. This may also be included in the digital computer. Address selector 33 provides the data for the two sets in pairs to be combined. Adder 41 is provided with a storage location for one beam data signal to retain the first of each pair and then adds the second to the first before passing the new combined data on to processor 35. It will be understood that other means of combining the data may be employed. For instance an individual reconstruction of absorption coefficients may be derived for each pair of "opposite" parallel sets (e.g. 180° and 0°) and the two pictures combined on display or otherwise. The term "combination of the data" is intended to include all such combination.

As described in U.S. Pat. No. 3,924,129 unit 35 shown in FIG. 3 may be provided as a suitable programmed digital computer. In a practical example of the invention the functions of units 33, 34, 41 and 35 may all be provided by a single digital computer. However they have been shown in FIG. 3 as separate units in order that their functions may be more clearly distinguished.

Figure 6:
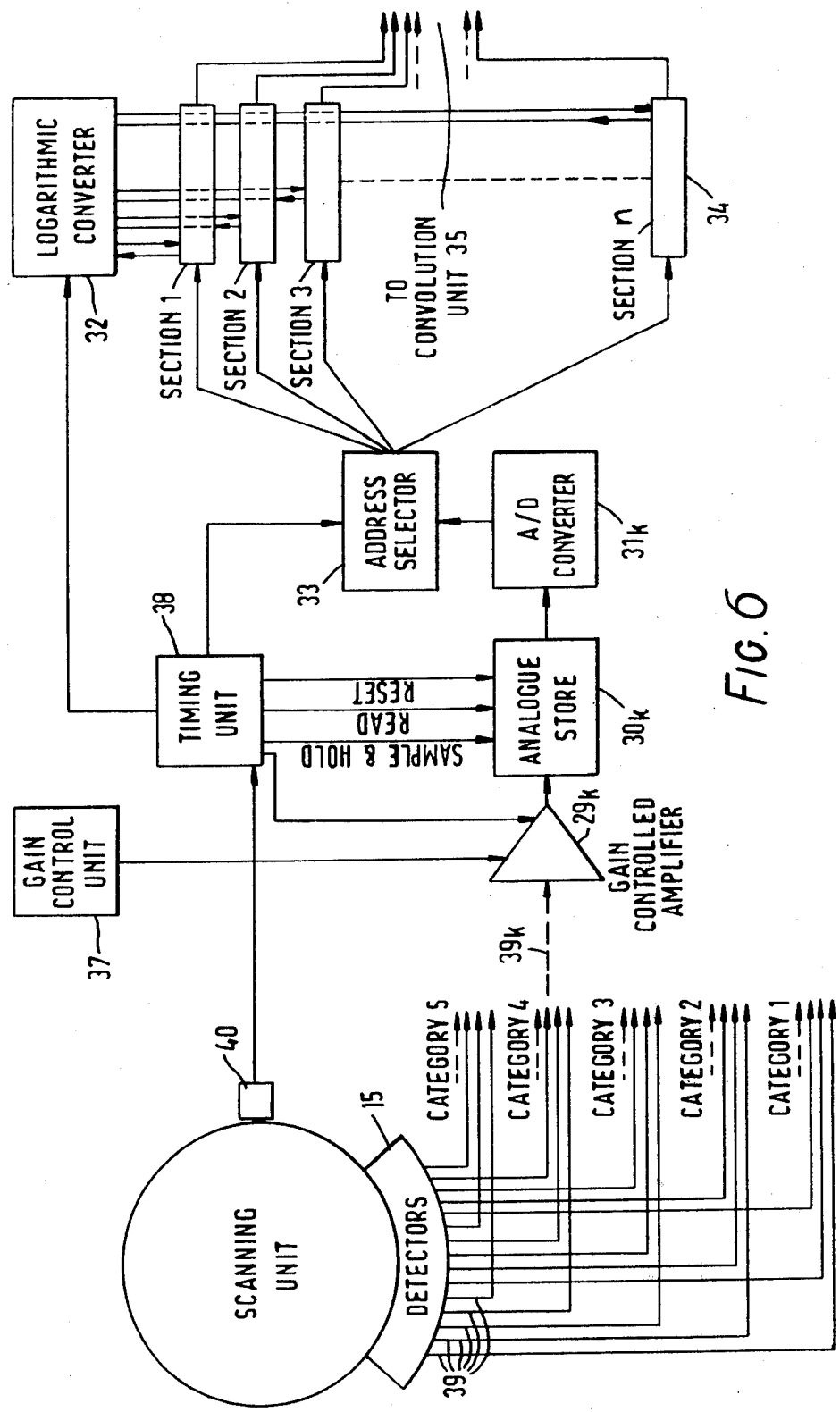

Instead of using a general purpose digital computer to perform the function of sorting the data into "parallel" sets, a special purpose computer may be employed. An example of such an arrangement is shown in FIG. 6.

Disregarding for the moment the plurality of conductors 39, divided into five categories, conductor $39_k$ transmitting output signals from a detector $k$ will be considered to be typical of all conductors from such detectors.

As mentioned hereinbefore, the duration of sampling of the output of each detector such as $k$ is such that the effective beam width, resulting from the orbital movement is that desired. In practice an "aperture effect" wil cause the beam width to be greater than this so that some overlap is provided as described, for example, in U.S. Pat. application Ser. No. 471,658 filed May 20, 1975 (Hounsfield), now abandoned in favor of U.S. application No. 608,204 filed Aug. 27, 1975, now U.S. Pat. No. 4,002,911. The output is amplified by amplifier $29_k$ controlled by gain control unit 37. Analogue store $30_k$ is the Miller integrator referred to hereinbefore operating in its known role of an analogue store used to sample and hold, thereafter to be reset to be available for further sampling in the same manner. A/D converter $32_k$ also operates as in FIG. 3. In response to address selector 33 the data are distributed to store 34 which in this case is divided into sections 1, 2, 3 ... n. All the data from conductors such as $k$ are also distributed to these sections of store 34. However in this example each section of store 34 holds the data of one "parallel" set corresponding to a diagonal of FIG. 5. Thus this circuit is unlike that of FIG. 3 which accepts data as desired and perform the sorting into parallel sets as a timing disassociated from that of the scanning. The FIG. 6 circuit requires data to be distributed to sections of store 34 and hence into "parallel" sets as they are derived and therefore the timing must be coordinated with the scanning. For this purpose address selector 33 is controlled by timing unit 38 which receives input signals from scanning timing signal unit 40. Timing unit 38 is also used to control the integrators 30.

For the purpose of combining data for beams at 180° relation of scan it should be noted that although data for the first 180° of scan are applied to the sections of store 34 in one order those for the second 180° (i.e. of the parallel sets, not of the scanning position) are applied in the reverse order to effect the combination described with respect to FIG. 4b. For this purpose address selector 33 is suitably programmed. When any section of store 34 has received all the data for its parellel set that data is transferred serially to convolution unit 35 for processing as referred to hereinbefore.

Log converter 32 could be provided between converter 31 and selector 33 in this example as in FIG. 3. However it has been shown cooperating with store 34 to withdraw data from respective storage locations, convert to logarithmic form and replace them in the same storage location. In this manner it is possible to provide a log converter to operate on one signal at a time instead of on several simultaneously as in FIG. 3. For the purpose described log converter 32 is controlled by timing control 38.

Considering the outputs from detector means 15 in FIG. 6 it will be seen that they are grouped into five categories. This feature, which is optional, enables the number of integrators to be reduced by one fifth although each channel should still have its own amplifier. In this arrangement the detectors are divided so that the first, sixth, eleventh etc. are allocated to category one, the second, seventh etc. to category two, the third etc. to category three, the fourth etc. to category four and the fifth etc. to category five. Thus the detectors of the five categories are interlaced. The data is derived from these detectors in conjunction with 2/15° orbital movements as follows. During the first 2/15° all detectors of category one are sampled. During the next 2/15° all detectors of category two are sampled for beam paths parallel to those used by the category one detectors. In the next 2/15° the detectors of category three are sampled and so on. In the sixth 2/15° the detectors of category one are sampled again for beam paths 2/3° displaced from those previously used for all five categories. Thus data for 2/3° spaced parallel sets are derived but with five times the number of beam paths otherwise possible for the number of integrators provided. For this purpose each integrator takes one corresponding beam from each category (e.g. all fifth position beams). Each amplifier is gated by timing unit 38 to provide data to the integrator only as required. The gating may be provided otherwise if required, for example the detector photomultipliers may be so gated or independent gates or switches provided.

It will be understood that the features of the present invention may be utilised with any signal processing such as that described in U.S. Pat. No. 3,778,614. Furthermore the invention may be utilised with scanning arrangements other than that described hereinbefore. For example the rotation need not be the simple rotation described but may be a more complex movement if desired for other purposes. In relation to the scanning arrangements described the examples of beam widths and spacings which have been given may be varied as desired provided the correct relationships are maintained. Furthermore each beam may be examined by more than one detector if desired.

What I claim is:

1. An apparatus, for examining a body by means of penetrating radiation, including means for generating output signals, representative of the absorption suffered by the radiation in passage along respective beam paths through a region of the body, for processing to provide a representation of the distribution of absorption of the radiation in the region, and combining means for combining groups of output signals each group relating to at least two beam paths, chosen so that the beam baths pass through a common elemental area of the region from different directions, to provide composite output signals representing the absorption of the radiation in passage through the body along composite beam paths of which the width varies differently from the widths of the component beam paths so that said processing can be effected on a plurality of output signals including at least some of said composite output signals.

2. Medical radiographic apparatus for examining a substantially planar section of the body of a patient, comprising a support for said body, a frame mounted for rotation about an axis extending generally longitudinally of said body, a source of X-rays supported by said frame for producing a spread of X-rays diverging from said source substantially in a plane at right angles to said axis so as to irradiate said section of said body, a plurality of detectors supported by said frame and adapted to receive radiation from said source after passing through said body, said detectors receiving radiation along respective narrow beam paths angularly distributed across said spread of X-rays, means for rotating said frame relative to said support for the patient about said axis through at least approximately one revolution, circuits for measuring radiation received by the respective detectors to provide beam data signals related to the radiation received by the respective detectors at successive angular positions assumed by said spread of X-rays relative to said body, a selector for selecting among said beam data signals different sequences of signals, each sequence of signals relating to radiation transmitted through said body along a parallel set of beam paths and the different sequences of signals corresponding to sets of beam paths angularly distributed about said axis and a circuit for providing a representation of the distribution of a characteristic of said section of the body with respect to radiation, said representation combining the effect of beam data signals relating to beam paths which are substantially coincident but of opposite direction.

3. Medical radiographic apparatus comprising:
means defining a patient position and means for generating a fan of radiation which diverges in moving away from the source in a substantially planar region intersecting the patient position;
means for orbiting the fan within said region around an axis located within the patient position over at least one revolution;
means for detecting the radiation emerging from the patient position in said region along a plurality of radiation beam paths which are within said fan or radiation and are at an angle to each other in said region to obtain a corresponding measurement signal for each of said beam paths;
means for combining the measurement signals for beam paths which are substantially coincident but at opposite directions to derive a corresponding combined measurement signal, and
means for processing the combined measurement signals to derive a representation of the distribution in said region of a radiation response characteristic of the matter traversed by said beam paths.

4. Medical radiographic apparatus as in claim 3 including means for selecting, from said combined measurement signals, sets of combined signals which correspond to sets of beam paths wherein the beam paths within each set are substantially parallel to each other and wherein the processing means include means for processing said sets of measurement signals in accordance with a convolution function.

5. A medical diagnostic X-ray machine for examining a slice of a patient which extends along a planar section through the patient, comprising:
means for supporting the patient;
means for generating X-radiation directed at the patient and propagating along said section from each of a number of locations distributed along at least one substantially full orbit around the patient and means for detecting the X-radiation after passage through the patient along each of a number of fan-shaped distributions of beam paths, each distribution originating at a respective one of said locations and fanning out therefrom along said section into angularly spaced beam paths whose center-to-center spacing in the patient is substantially less than twice the width of a beam path in the plane of the section, and for producing output signals each related to the amount of radiation which has passed through the patient along a respective one of said beam paths, the relative arrangement of the locations at which the distributions originate causing radiation from the X-ray generating means to travel along the line of each beam path in opposite directions, once from one location and once from another; and
means for forming a set of picture element signals from the output signals relating to locations distributed along about the whole of said orbit, each picture element signal representing the X-ray response of a respective one only of the elements into which the patient slice is divided by a finite Cartesian matrix notionally superimposed on the slice to form thereby a composite picture of the anatomy of the examined slice of the patient and means for displaying said composite picture.

6. A medical diagnostic X-ray machine as in claim 5 in which the means for generating X-radiation comprise means for generating from each of said locations a fan-shaped distribution of beam paths which is wide enough to encompass the entire patient slice and the detecting and producing means comprise means for substantially concurrently detecting the radiation along all of the beam paths of a fan-shaped distribution and for producing output signals related to the radiation along each of the beam paths of the distribution.

7. A medical diagnostic X-ray machine as in claim 6 in which the forming means comprise means for forming picture element signals each of which is a measure of the X-ray attenuation coefficient of a respective element of the patient slice.

* * * * *

UNITED STATES PATENT AND TRADEMARK OFFICE
CERTIFICATE OF CORRECTION

PATENT NO. : 4,126,787

DATED : November 21, 1978

INVENTOR(S) : GODFREY N. HOUNSFIELD

It is certified that error appears in the above-identified patent and that said Letters Patent are hereby corrected as shown below:

Page 1, col. 1, between items "[60]" and "[51]", insert:

--[30] Foreign Application Priority Data
Jan. 31, 1974 United Kingdom ---- 4562/74 --.

Col. 1, line 28, delete "on" and insert -- an --.

Col. 1, line 29, delete "impositions" and insert -- dispositions --.

Col. 1, line 60, delete "3,773,614" and insert -- 3,778,614 --.

Col. 1, line 63, delete "cr" and insert -- or --.

Col. 2, line 66, delete "subjet" and insert -- subject --.

Col. 3, line 22, delete "team" and insert -- beam --.

Col. 4, line 17, delete "ray" and insert " may --.

Col. 4, line 51, delete "centralines" and insert -- centrelines --.

UNITED STATES PATENT AND TRADEMARK OFFICE
CERTIFICATE OF CORRECTION

PATENT NO. : 4,126,787  
DATED : November 21, 1978  
INVENTOR(S) : GODFREY N. HOUNSFIELD It is certified that error appears in the above-identified patent and that said Letters Patent are hereby corrected as shown below:

Col. 4, line 59, delete "joint" and insert -- point --.

Col. 4, line 65, delete "lock-up" and insert -- look-up --.

Col. 5, line 36, delete "contrelines" and insert -- centrelines --.

Col. 7, line 34, delete "wil" and insert -- will --.

Col. 7, line 46, delete "$32_k$" and insert -- $31_k$ --.

Col. 8, line 11, delete "location" and insert -- locations --.

Signed and Sealed this

Sixth Day of November 1979

[SEAL]

Attest:

RUTH C. MASON  
Attesting Officer

LUTRELLE F. PARKER  
Acting Commissioner of Patents and Trademarks